US009327976B2

(12) United States Patent
Landi et al.

(10) Patent No.: US 9,327,976 B2
(45) Date of Patent: May 3, 2016

(54) PLURISUBSTITUTED HYDROXYAPATITE AND THE COMPOSITE THEREOF WITH A NATURAL AND/OR SYNTHETIC POLYMER, THEIR PREPARATION AND USES THEREOF

(75) Inventors: Elena Landi, Dozza-Toscanella (IT); Anna Tampieri, Faenza (IT); Giancarlo Celotti, Faenza (IT); Simone Sprio, Bologna (IT); Daniele Pressato, Montegrotto Terme (IT); Claudio De Luca, Padua (IT)

(73) Assignees: C.N.R. CONSIGLIO NAZIONALE DELLE RICERCHE, Rome (IT); FIN-CERAMICA FAENZA S.P.A., Faenza (Ravenna) (IT)

( * ) Notice: Subject to any disclaimer, the term of this patent is extended or adjusted under 35 U.S.C. 154(b) by 510 days.

(21) Appl. No.: 12/089,887

(22) PCT Filed: Oct. 12, 2006

(86) PCT No.: PCT/IB2006/002844
§ 371 (c)(1), (2), (4) Date: Apr. 10, 2008

(87) PCT Pub. No.: WO2007/045954
PCT Pub. Date: Apr. 26, 2007

(65) Prior Publication Data
US 2008/0262121 A1    Oct. 23, 2008

(30) Foreign Application Priority Data
Oct. 18, 2005  (IT) .............................. MI2005A1966

(51) Int. Cl.
*C01B 25/32*   (2006.01)
*A61L 27/12*   (2006.01)
(Continued)

(52) U.S. Cl.
CPC ............... *C01B 25/322* (2013.01); *A61L 27/12* (2013.01); *A61L 27/46* (2013.01); *C01B 25/16* (2013.01); *A61F 2/28* (2013.01); *A61F 2310/00293* (2013.01)

(58) Field of Classification Search
USPC ................. 423/305, 306, 307, 308, 309, 311; 623/16.11, 23.56, 923; 106/462, 690; 427/2.27; 606/76, 77; 264/16, 19; 424/444; 523/115
See application file for complete search history.

(56) References Cited

U.S. PATENT DOCUMENTS 6,312,468 B1   11/2001   Best et al.
6,338,810 B1   1/2002    Carpena et al.
(Continued)

FOREIGN PATENT DOCUMENTS

EP    1 362 565 A1    11/2003
EP    1518569 A1 *   3/2005
(Continued)

OTHER PUBLICATIONS

Takashi et al. (JP 2002-137914 A) translation, May 14, 2002.*
(Continued)

*Primary Examiner* — Melissa Swain
(74) *Attorney, Agent, or Firm* — Silvia Salvadori, P.C.; Silvia Salvadori

(57) ABSTRACT

The present invention relates to a hydroxyapatite multi-substituted with, physiologically compatible ion species and to its biohybrid composite with a natural and/or synthetic polymer, which are useful in the preparation of a biomimetic bone substitute for treating bone tissue defects. Furthermore, the present invention relates to a method for their preparation and uses.

21 Claims, 6 Drawing Sheets

CONDUCTIVITY COMPARISON

Figure 1:
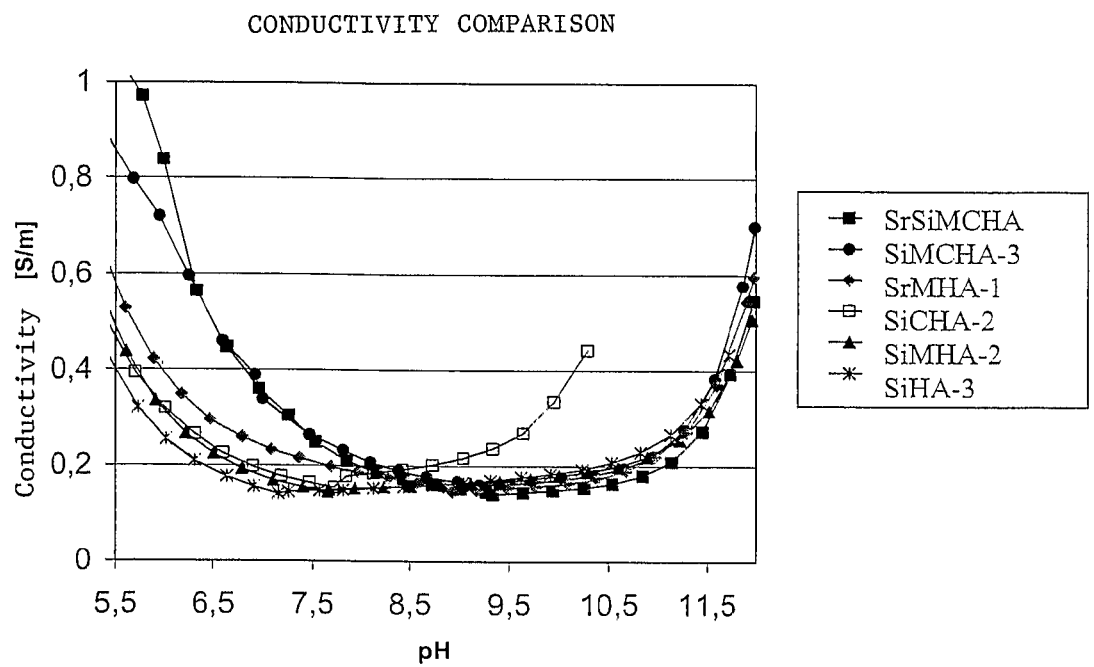

(51) Int. Cl.
*A61L 27/46* (2006.01)
*C01B 25/16* (2006.01)
*A61F 2/28* (2006.01)

(56) References Cited

U.S. PATENT DOCUMENTS

| | | | |
|---|---|---|---|
| 7,494,950 B2 * | 2/2009 | Armitage et al. | 501/95.2 |
| 2004/0078087 A1 | 4/2004 | Kim et al. | |
| 2004/0082998 A1 | 4/2004 | Shinomiya et al. | |
| 2004/0170699 A1 * | 9/2004 | Chane-Ching et al. | 424/602 |
| 2005/0208097 A1 * | 9/2005 | Li | 424/423 |

FOREIGN PATENT DOCUMENTS

| | | |
|---|---|---|
| JP | 07 275343 A | 10/1995 |
| JP | 2002 137914 A | 5/2002 |
| WO | WO 98/08773 A1 | 3/1998 |
| WO | WO 99/33766 A1 | 7/1999 |
| WO | WO 2004/044274 A1 | 5/2004 |
| WO | WO 2005/082780 A1 | 9/2005 |

OTHER PUBLICATIONS

Soulet et al., "Simulation of the α-annealing effect in apatitic structures by He-ion irradiation: Influence of the silicate/phosphate ratio and of the OH−/F− substitution," Nov. 2001, Nuclear Instruments and Methods in Physics Research Section B: Beam Interactions with Materials and Atoms, vol. 184, Issue 3, pp. 383-390.*

Vignoles et al, Influence of Preparation Conditions on the Composition of Type B Carbonated Hydroxyapatite and on the Localization of the Carbonate Ions, Calcified Tissue International (1988) 43:33-40.*

Database CA [Online] Chemical Abstracts Service, Columbus, Ohio, US; "Manufacture of artificial bone for surgical or dental use", XP002422626, retrieved from STN, Database accession No. 124:97814, abstract.

Kanno Tohru et al.: "Characteristics of the carbonate ions incorporated into calcium-, partially-strontium-substituted and strontium apatites", J Mater Sci Lett; Journal of Materials Science Letters, Aug. 15, 1999, Kluwer Academic Publishers, Dordrecht, Netherlands, vol. 18, No. 16, Aug. 15, 1999, pp. 1343-1345, XP002422622.

Database WPI Week 200265, Derwent Publications Ltd., London, GB; AN 2002-602271, XP002422663.

Kim S R et al.: "Synthesis of Si,Mg substituted hydroxyapatites and their sintering behaviors", Biomaterials, Elsevier Science Publishers BV., Barking, GB, vol. 24, No. 8, Apr. 2003, pp. 1389-1398, XP004401472, ISSN: 0142-9612.

Bacquet G et al.: "F<+F> centre in (Ca—Sr) carbonated hydroxyapatites", Radiation Effects UK, vol. 72, No. 1-4, 1983, pp. 299-302, XP002422623, ISSN: 0033-7579.

Rhee Sang-Hoon et al.: "Synthesis of a hydroxyapatite/collagen/chondroitin sulfate nanocomposite by a novel precipitation method", Journal of the American Ceramic Society, American Ceramic Soc. Westerville, OH, USA, vol. 84, No. 2, Feb. 2001, pp. 459-461, XP002423163.

Girija E K et al.: "Effect of poly L-aspartic acid on the biomimetic formation of calcium phosphate on collagen gel", Key Eng Mat; Key Engineering Materials 2002, vol. 218-220, Nov. 14, 2001, pp. 113-116, XP008076050.

* cited by examiner

PLURISUBSTITUTED HYDROXYAPATITE AND THE COMPOSITE THEREOF WITH A NATURAL AND/OR SYNTHETIC POLYMER, THEIR PREPARATION AND USES THEREOF

The present invention relates to a hydroxyapatite multi-substituted with physiologically compatible ion species and to its biohybrid composite with a natural and/or synthetic polymer, which can be used in the preparation of a biomimetic bone substitute for treating bone tissue defects.

Moreover, the present invention relates to a method for their preparation and uses.

Hydroxyapatite is a calcium phosphate regarded as one of the most useful materials as bone substitutes and/or implants, since it is an essential constituent of the mineral/inorganic part of mammals' bones and teeth. Said inorganic part was represented for a long time as stoichiometric hydroxyapatite, $Ca_{10}(PO_4)_6(OH)_2$. Actually, the physiological inorganic phase of bones and teeth is not made up of a stoichiometric calcium phosphate only, or hydroxyapatite (for simplicity's sake referred to below as HA), as mentioned above. As a matter of fact, physiological hydroxyapatite, which is present in bones and teeth, comprises in its structure also a certain amount of chemical substitutions, both anionic and cationic, which on one hand make it more reabsorbable by the living organism and on the other hand give it a higher ability to stimulate the growth of new bone tissue than stoichiometric hydroxyapatite. Said ion substituents, though present in small amounts, can be connected to the specific biological properties of physiological hydroxyapatite and play a primary role in the biochemistry of bone, enamel and dentine.

The presence of these ion substituents is therefore fundamental in order to obtain a biomaterial which, by reproducing in an optimal manner (and possibly better) the biostructure and biochemistry of natural bone tissue, can integrate and replace it, with very short bone integration and regeneration times, with respect to conventional stoichiometric hydroxyapatite (which, as such, is re-absorbed in too long times and causes an insufficient osteoblast activation).

Among the most important ion substituents, which are present in physiological hydroxyapatite, the following can be mentioned:

on one hand, silicate and carbonate anions, which partially substitute phosphate ions (in the so-called "site B" of HA);

on the other hand, $Mg^{2+}$ and $Sr^{2+}$ cations, which partially substitute calcium ions.

Moreover, carbonate ion partially substitutes also $OH^-$ ions of site A of HA, thus resulting in a partial substitution in both sites A and B thereof, mainly in phosphate position (site B) with respect to hydroxyl position (site A). As a matter of fact, in physiological HA both A-type and B-type carbonations are present, in a mutual molar ratio A/B of about 0.7 to about 0.9 (corresponding to a percent molar ratio A/B of about 70% to about 90%), depending on the individual's species and age.

Silicon is one of the essential trace elements in biological processes. The importance of silicon for bone formation and calcification was proved by in-vitro and in-vivo scientific studies. For instance, the substitution of phosphate ions with silicate ions in hydroxyapatite increases the activity of osteoblast cells with respect to stoichiometric hydroxyapatite. As a matter of fact, a higher bone deposition and a faster bone remodeling were observed on the surface of implants of HA replaced with silicate ions (for simplicity's sake, silicon-hydroxyapatite, SiHA), with respect to stoichiometric HA. Silicon content in biological apatite varies approximately of 0.2 to 0.8% by weight.

The presence of silicon seems to promote also cell adhesion and the formation of bone organic part, in particular of collagen.

As far as magnesium is concerned, it seems to play an important role in quality modifications of bone matrix resulting in the fragility thereof. The lack of $Mg^{2+}$ negatively affects all the stages of skeleton metabolism, causing the stop of bone growth, the reduction of osteoblast and osteocyte activity, osteopoenia and bone fragility.

Moreover, synthetic hydroxyapatite substituted with $Mg^{2+}$ (for simplicity's sake, MgHA) is more soluble and therefore more reabsorbable than unsubstituted HA. However, there is a limit to the incorporation of $Mg^{2+}$ in HA, since high concentrations of said ion tend to destabilize its structure. Molar ratios $Mg^{2+}/Ca^{2+}$ above 0.3 make proportionally likely the formation of tricalcium magnesium phosphate to the detriment of MgHA. Anyway, the substitution of $Ca^{2+}$ ion with $Mg^{2+}$ can be advantageously increased by simultaneously incorporating carbonate ions into the phosphate site (site B) of apatite structure, As such, carbonate ion is already normally present in the structure of physiological HA in an amount of 3% to 8% by weight, with respect to the weight of HA, depending on the individual's age.

Synthetic carbonations should therefore be carried out preferably in site B, also because A-type carbonation results in a lower affinity of apatite towards osteoblast cells, giving rise to a lower cell adhesion and to a low collagen production, with respect to unsubstituted HA. It would therefore be advantageous to direct HA carbonation specifically only in its site B. As far as $Sr^{2+}$ ion is concerned, its presence varies depending on age, tissue and physical exercise. The molar ratio $Sr^{2+}/Ca^{2+}$ in physiological HA is generally of 0.02 to 0.30, higher values being associated with young bone. Moreover, $Sr^{2+}$ has a stabilizing effect on apatite structure.

The presence of each specific ion in convenient amounts gives a particular contribution to the biological process of bone remodeling, and further varies the characteristics of solubility, reabsorption, stability and mechanical resistance of substituted HA thanks to the large number of crystal defects due to their presence. All ion substitutions which are naturally present in physiological HA therefore contribute to determine the specific biological characteristics of bone tissue.

It would therefore be extremely important to have a synthetic material which is able to reproduce in an optimal manner (and possibly better) the characteristics given to bone tissue by its complex physiological inorganic component (apatite), so as to obtain completely biocompatible and biomimetic bone substitutes to be used for treating bone defects.

Unfortunately, a material meeting satisfactorily the characteristics referred to above is not known.

It is therefore still necessary to have a material as the one described above, which is completely biocompatible and biomimetic, whose reabsorbability and osteogenesis characteristics are such as to make it an optimal substitute of the inorganic component of natural bone tissue.

The aim of the present invention is to give a suitable answer to the need disclosed above.

This aim and others, which will be evident from the following detailed description, have been achieved by the Applicant, who has unexpectedly found that a hydroxyapatite substituted with an effective amount of silicate and/or $Sr^{2+}$ ions and at least one physiologically compatible ion species, selected among carbonate, $Mg^{2+}$ and/or mixtures thereof, can give a suitable answer to the problems referred to above.

Therefore, an object of the present invention is a hydroxyapatite multi-substituted with an effective amount of silicate and/or $Sr^{2+}$ ions and, additionally, with at least one other physiologically compatible ion species, as disclosed in the appended independent claim.

Another object of the present invention is a method for preparing the above compound, whose characteristics are disclosed in the appended independent claim. A further object of the present invention is the use of the above compound for preparing a bone substitute, as disclosed in the appended independent claim.

Still another object of the present invention is the bone substitute obtained with the above compound, as disclosed in the appended independent claim.

Preferred embodiments of the present invention are disclosed in the appended dependent claims.

Among these, a particularly preferred object of the present invention is a biohybrid composite comprising the above hydroxyapatite and further comprising a convenient amount of a natural and/or synthetic polymer, as well as a method for preparing said biohybrid composite.

Figure 2:
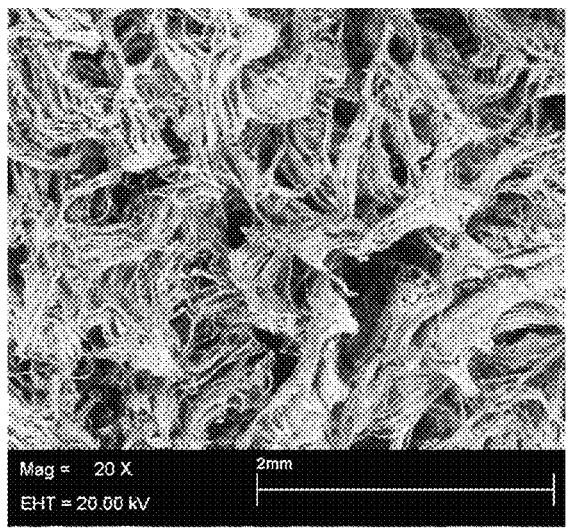
Figure 2:
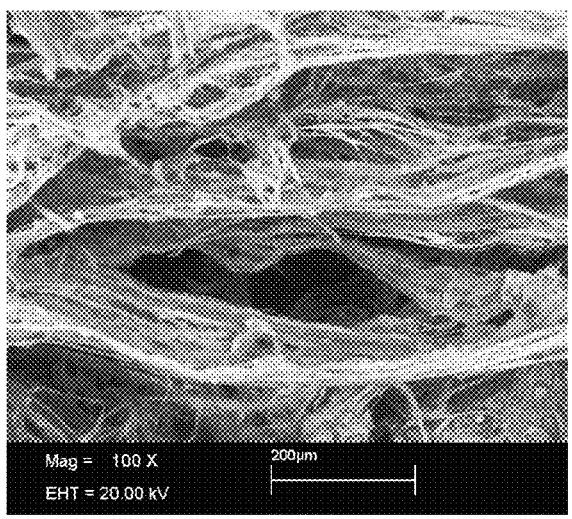
Figure 2:
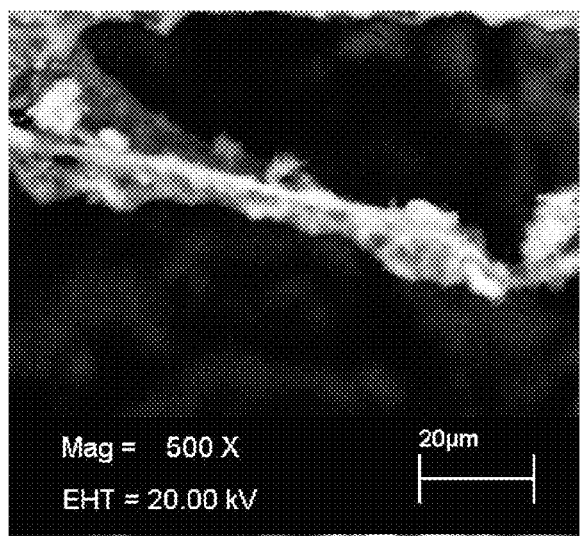
Figure 3:
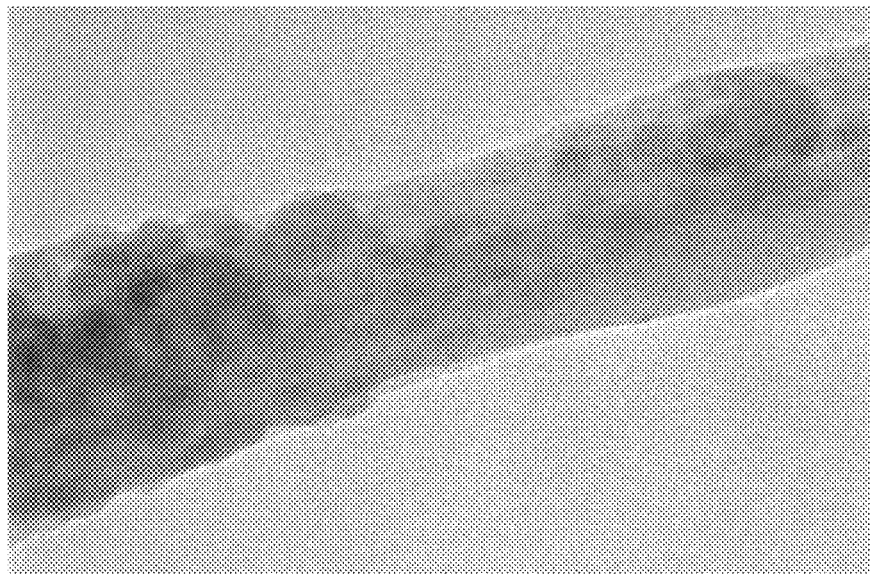
Figure 3:
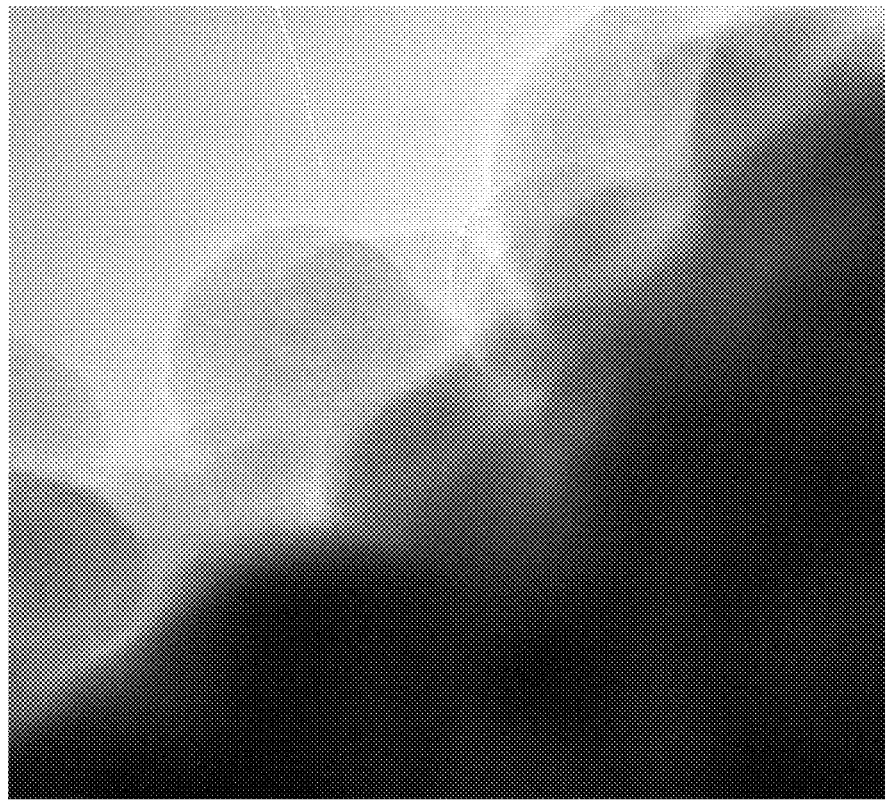
Figure 4:
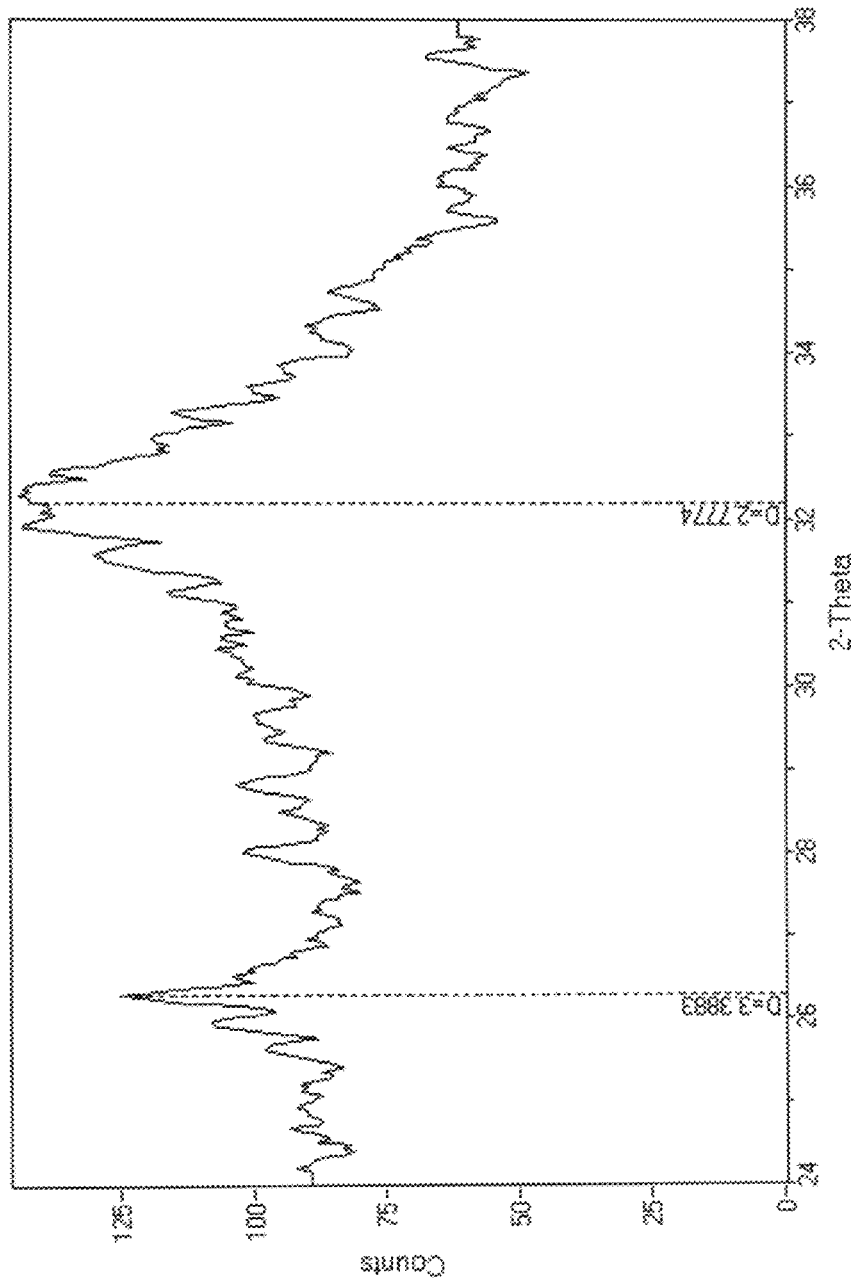
Figure 5:
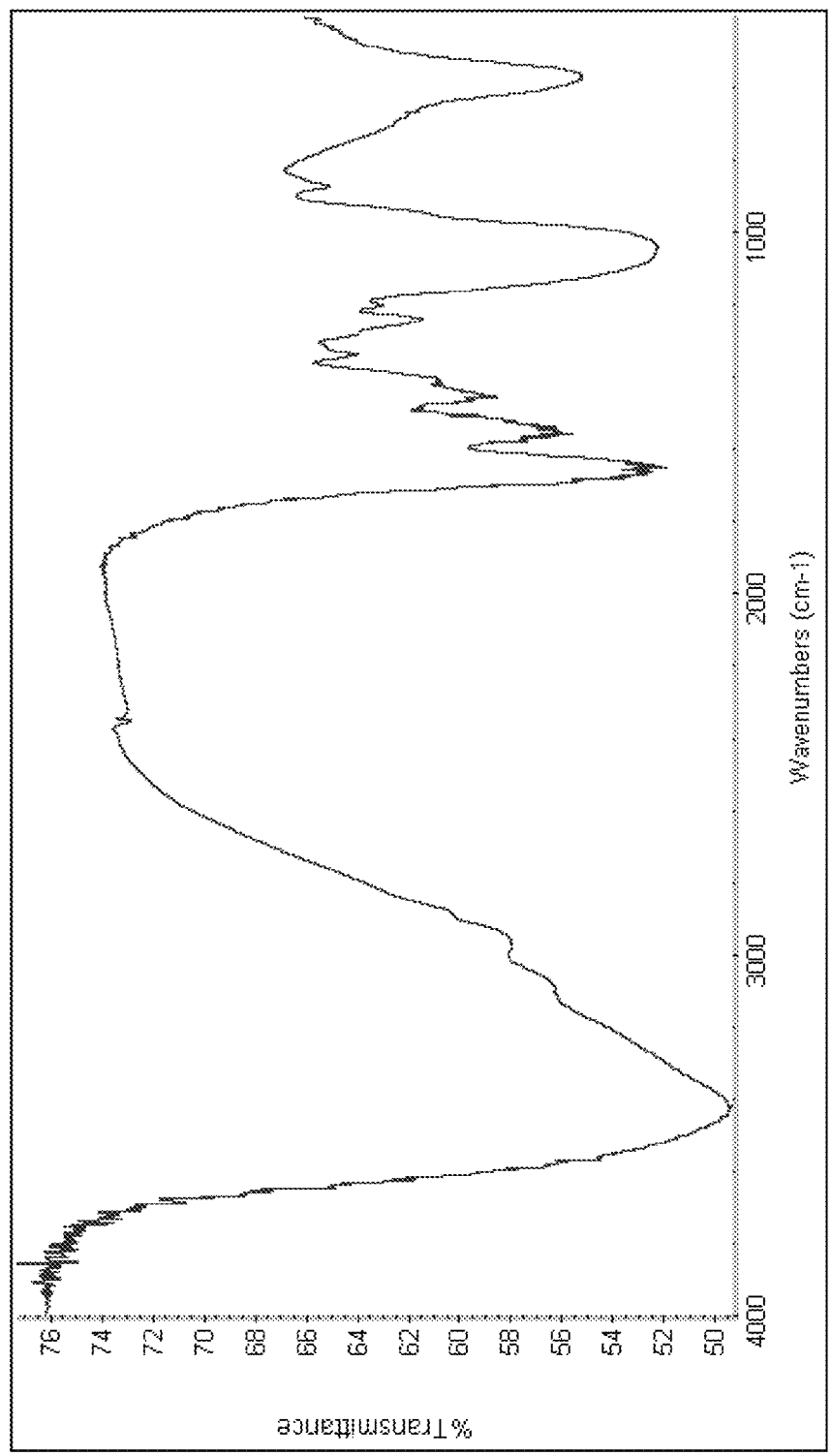
Figure 6:
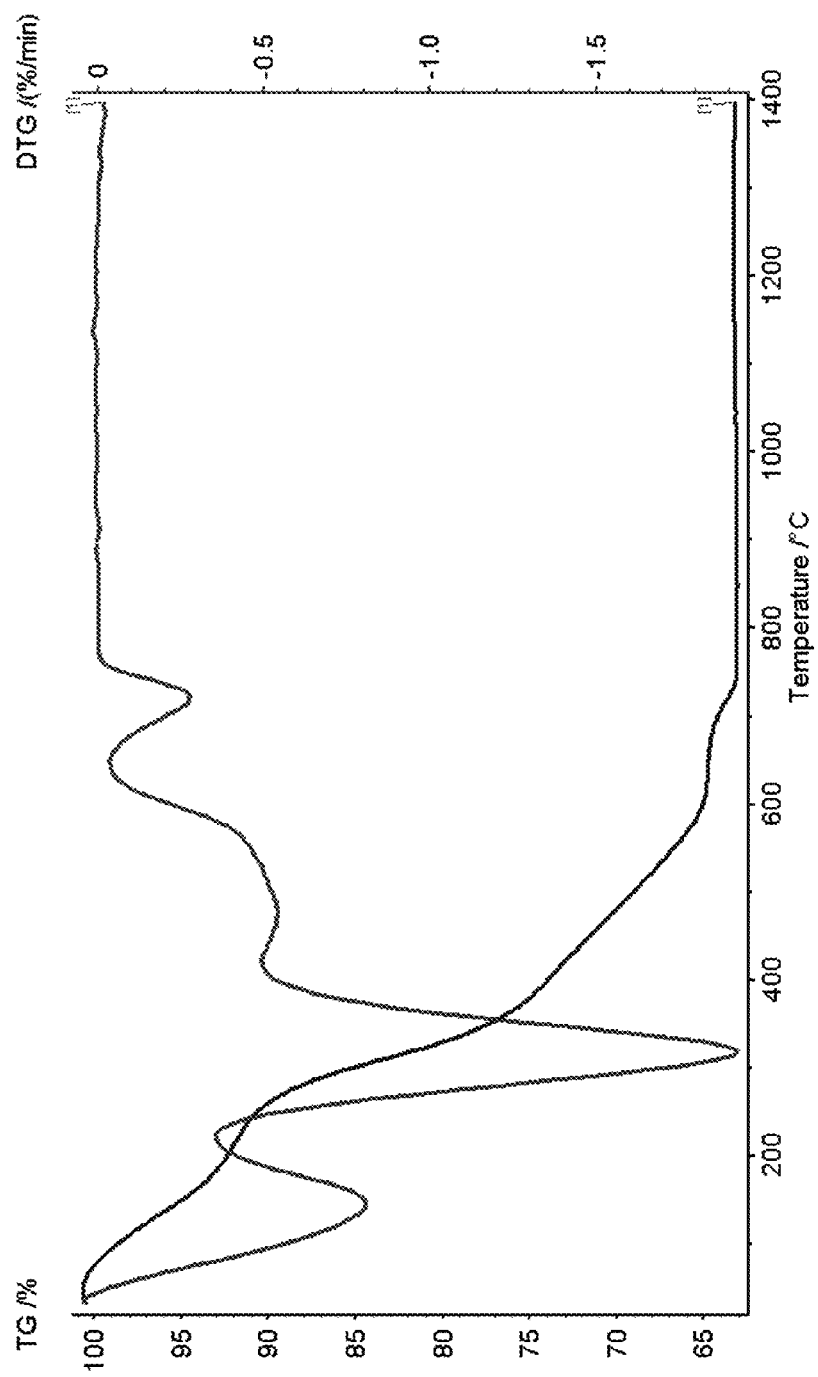

The present invention is disclosed in detail in the following description. Moreover, it is further disclosed in some of its preferred aspects by the accompanying FIGS. 1 to 6, in which:

FIG. 1 shows the comparison between the pH-depending trend of water conductivity of a given number of (aqueous) suspensions of the powders of multi-substituted hydroxyapatites according to the present invention;

FIG. 2 shows an ESEM (Environmental Scansion Electronic Microscopy) analysis of a composite (is_SrSiMgCHA/Coll 70/30 SBF, described in Example 2 disclosed below) according to the present invention, made up of an inorganic phase of multi-substituted hydroxyapatite (SrSiMgCHA), which is incorporated during its synthesis into the collagen phase in the self-assembly process of the latter (in-situ direct nucleation); the composite is characterized by a porous structure comprising pores with extremely variable size; both macropores with size above 300 µm, which enable the penetration of osteoblasts, and micromesopores, which enable the permeation of the whole structure by physiological fluids, can be seen;

FIG. 3 shows a TEM (Transmission Electron Microscopy) analysis of a composite according to the present invention (is_SrSiMgCHA/Coll 70/30 SBF), from which it can be inferred that the in-situ nucleation process of apatite in collagen enables to reduce composite particle size with respect to what can be obtained with chemical doping (substitution) of the inorganic phase only; as a matter of fact, whereas multi-substituted hydroxyapatites as such have a size of 20 nm to 40 nm, depending on doping ions, with in-situ collagen nucleation multi-substituted apatites with nucleuses having a size of 5 nm to 10 nm are generated;

FIG. 4 shows a XRD (X-Ray Diffraction; Cu Kα radiation) analysis of a composite according to the present invention (is_SrSiMgCHA/Coll 70/30 SBF); the spectrum is typical of a phase with low crystallinity, however, the characteristic peaks of apatite phase (002) at about 26 degrees of 2-Theta, (211) and (112) can be identified, which tend to create one band including the peak at (300), around 32 degrees of 2-Theta (Theta is the angle between incident X ray and X ray diffracted by the sample: as a rule, it is the abscissa of a X-ray diffractogram); spectrum appearance is consistent with the composition of the material made up of an organic phase (collagen) and of an inorganic phase (multi-substituted apatite) with an extremely small crystallites size;

FIG. 5 shows a FTIR (Fourier Transformed Infra Red Spectroscopy) analysis of a composite according to the present invention (is_SrSiMgCHA/Coll 70/30 SBF), in which carbonate bending in site B (874 $cm^{-1}$) and collagen $coo^-$ stretching, displaced towards lower wavenumber values (from 1340 to about 1336.5 $cm^{-1}$), point out a close interaction between apatite and collagen; this confirms apatite nucleation inside and on collagen fibers, contrary to what occurs when the preformed apatite phase is mixed into the collagen phase (in this case, the two phases remain distinct);

FIG. 6 shows a TGA (thermogravimetric curve and its derivative, extracted from STA analysis: STA includes TGA and DTA, i.e. thermogravimetric analysis+thermodifferential analysis) analysis of a composite according to the present invention (is_SrSiMgCHA/Coll 70/30 SBF); the curve of weight loss enables to evaluate the relative amount of apatite and collagen phases; the composite apatite/collagen 70/30 is characterized by an actual weight ratio apatite/collagen of about 67/33; as a matter of fact, if we consider that the apatite phase alone is characterized by a weight loss depending on its stoichiometry (generally of about 10-15%—adsorbed, occluded water, carbonation and so on), the relative content of the collagen phase can be inferred from the total weight loss of the composite; the weight content of carbonate in apatite is inferred from the weight loss ($CO_2$ elimination as a result of the decarbonation process) in the range 600-1000° C.

The present invention relates to a hydroxyapatite (or non-stoichiometric hydroxyapatite, for convenience's sake also referred to as nsHA) multi-substituted with physiologically compatible ion species, in which said hydroxyapatite comprises an effective amount of silicate and/or $Sr^{2+}$ ions and, additionally, at least one ion species selected among: carbonate, $Mg^{2+}$ and/or mixtures thereof.

In said hydroxyapatite referred to above:
the molar ratio of silicate ions to phosphate ions of hydroxyapatite is of 0.001 to 0.25, corresponding to a percent $SiO_4/PO_4$ of 0.1% to 25%; and
the molar ratio of $Sr^{2+}$ ions to $Ca^{2+}$ ions of hydroxyapatite is of 0.002 to 0.35, corresponding to a percent molar ratio Sr/Ca of 0.2% to 35%.

Preferably, said ratio of silicate to phosphate is of 0.005 to 0.20, corresponding to a percent molar ratio $SiO_4/PO_4$ of 0.5% a 20%.

More preferably, said ratio of silicate to phosphate is of 0.01 to 0.10, corresponding to a percent molar ratio $SiO_4/PO_4$ of 1% a 10%.

In its turn, said ratio of $Sr^{2+}$ to $Ca^{2+}$ is preferably of 0.02 to 0.30, corresponding to a percent molar ratio Sr/Ca of 2% to 30%.

More preferably, said ratio of $Sr^{2+}$ e $Ca^{2+}$ is of 0.03 to 0.25, corresponding to a percent molar ratio Sr/Ca of 3% to 25%.

In a preferred embodiment of the invention, said hydroxyapatite additionally comprises at least the carbonate ion.

Said carbonate is present in a molar ratio of carbonate to phosphate of hydroxyapatite of 0.01 to 0.80, corresponding to a percent molar ratio $CaCO_3/PO_4$ of 1.00% to 80%; preferably of 0.05 to 0.30, corresponding to a percent molar ratio $CaCO_3/PO_4$ of 5% to 30%.

In another preferred embodiment of the invention, said hydroxyapatite additionally comprises at least the $Mg^{2+}$ ion.

Said $Mg^{2+}$ is present in a molar ratio of $Mg^{2+}$ to $Ca^{2+}$ of hydroxyapatite of 0.01 to 0.30, corresponding to a percent molar ratio Mg/Ca of 1.00% to 30%; preferably, in a molar ratio of 0.03 to 0.20, corresponding to a percent molar ratio Mg/Ca of 3% to 20%.

In a further preferred embodiment of the invention, said hydroxyapatite additionally comprises a mixture of carbonate and $Mg^{2+}$ ions, wherein said ions are present in the same molar ratios as referred to above.

In some of the preferred embodiments of the invention, said hydroxyapatite comprises the following substituent ions:
   silicate, $Sr^{2+}$, carbonate; or
   silicate, $Sr^{2+}$, $Mg^{2+}$; or
   silicate, carbonate, $Mg^{2+}$; or
   $Sr^{2+}$ carbonate, $Mg^{2+}$,
wherein said ions are present in the same molar ratios as referred to above.

In a further preferred embodiment of the invention, said hydroxyapatite comprises substituent silicate, $Sr^{2+}$, carbonate and $Mg^{2+}$ ions, wherein said ions are present in the same molar ratios as referred to above; preferably, said ions are present in the following ratios:
   silicate ion is present in a molar ratio $SiO_4/PO_4$ of 0.01 to 0.10;
   $Sr^{2+}$ ion is present in a molar ratio Sr/Ca of 0.03 to 0.25;
   carbonate ion is present in a molar ratio $CO_3/PO_4$ of 0.05 to 0.30;
   $Mg^{2+}$ ion is present in a molar ratio Mg/Ca of 0.03 to 0.20.

In a particularly preferred embodiment of the invention, the multi-substituted hydroxyapatite consists of a hydroxyapatite substituted with: silicate, $Sr^{2+}$, carbonate (SrSiCHA), wherein said ions are present in the same molar ratios as referred to above.

In another particularly preferred embodiment of the invention, the multi-substituted hydroxyapatite consists of a hydroxyapatite substituted with: silicate, $Sr^{2+}$, $Mg^{2+}$ (SrSiMgHA), wherein said ions are present in the same molar ratios as referred to above.

In another particularly preferred embodiment of the invention, the multi-substituted hydroxyapatite consists of a hydroxyapatite substituted with: silicate, carbonate, $Mg^{2+}$ (SiMgCHA), wherein said ions are present in the same molar ratios as referred to above.

In another particularly preferred embodiment of the invention, the multi-substituted hydroxyapatite consists of a hydroxyapatite substituted with: $Sr^{2+}$, carbonate and $Mg^{2+}$ (SrMgCHA), wherein said ions are present in the same molar ratios as referred to above.

In a further particularly preferred embodiment of the invention, the multi-substituted hydroxyapatite consists of a hydroxyapatite substituted with: silicate, $Sr^{2+}$, carbonate and $Mg^{2+}$ (SrSiMgCHA), wherein said ions are present in the same molar ratios as referred to above.

Powders of multi-substituted HA according to the present invention were synthesized with a method conveniently studied and optimized so as to obtain results that are as much as possible similar to what occurs in nature.

Said method for preparing a multi-substituted hydroxyapatite according to the present invention includes neutralizing a basic aqueous suspension a) of $Ca(OH)_2$, comprising a convenient amount of silicate and/or $Sr^{2+}$ ions, by addition of an aqueous solution b) of $H_3PO_4$, wherein, in said neutralization reaction:
   i) said aqueous suspension a) further comprises an effective amount of $Mg^{2+}$ ions; and/or
   ii) the addition of said solution b) is carried out simultaneously to the addition of an aqueous solution of bicarbonate ions.

Said neutralization reaction was carried out at room or physiological temperature (of 20° C. to 40° C.; preferably of 25° C. to 37° C.). The whole synthesis is carried out under conditions of pH self-controlled at about 12 (thus avoiding continuous additions of basifying agents such as ammonia), ensuring the thermodynamic stability of the apatite phase with respect to calcium biphosphate, which competes therewith at low pH values.

The desired calcium and phosphate ion substituents of hydroxyapatite are introduced into the reaction environment by using as reagents suitable salts thereof, such as, preferably though not necessarily (other salts thereof can be used if desired): magnesium chloride, sodium bicarbonate, silicon tetraacetate, strontium nitrate, dissolved in the aqueous solution in convenient amounts.

Preferably, said salts and (initial) reagents are used at the following concentrations:
   $Ca(OH)_2$: 10 to 1000 g/l, preferably 30 to 250 g/l;
   $Si(CH_3COO)_4$: 5 to 500 g/l, preferably 8 to 70 g/l;
   $Sr(NO_3)_2$: 5 to 600 g/l, preferably 25 to 300 g/l;
   $MgCl_2\ 6H_2O$: 5 to 700 g/l, preferably 25 to 250 g/l;
   $H_3PO_4$: 5 to 1000 g/l, preferably 50 to 200 g/l;
   $NaHCO_3$: 2 to 600 g/l, preferably 8 to 70 g/l.

In a preferred embodiment, a suspension of calcium hydroxide is added (under stirring and at room or physiological temperature) with convenient amounts of solutions of silicon tetraacetate and/or strontium nitrate (and magnesium chloride, if desired).

Still under stirring, the necessary amount of orthophosphoric acid (and of sodium bicarbonate, if desired, dripping it separately from orthophosphoric acid) is dripped into the above suspension.

Table 1 contains by way of example the amounts of reagents used for the syntheses of some multi-substituted apatites according to the invention.

TABLE I

| | $Ca(OH)_2$ | $Si(CH_3COO)_4$ | $MgCl_2\ 6H_2O$ | $Sr(NO_3)_2$ | $H_3PO_4$ | $NaHCO_3$ |
|---|---|---|---|---|---|---|
| | | | Concentr. range of reagents | | | |
| | 10-1000 g/l pref.: 30-250 g/l | 2-500 g/l pref.: 8-70 g/l | 5-700 g/l pref.: 25-250 g/l | 5-600 g/l pref.: 25-300 g/l | 5-1000 g/l pref.: 50-200 g/l | 2-600 g/l; pref.: 8-70 g/l |
| SiHA-1 | 20 g in 600 ml $H_2O$ | 1.94 g in 200 ml $H_2O$ | — | — | 16.63 g in 200 ml $H_2O$ | — |
| SiHA-2 | 20 g in 600 ml $H_2O$ | 3.66 g in 200 ml $H_2O$ | — | — | 15.65 g in 200 ml $H_2O$ | — |
| SiHA-3 | 20 g in 600 ml $H_2O$ | 6.55 g in 200 ml $H_2O$ | — | — | 14.00 g in 200 ml $H_2O$ | — |
| SiCHA-1 | 20 g in 600 ml $H_2O$ | 1.94 g in 200 ml $H_2O$ | — | — | 16.63 g in 200 ml $H_2O$ | 8.12 g in 400 ml $H_2O$ |
| SiCHA-2 | 20 g in 600 ml $H_2O$ | 1.94 g in 200 ml $H_2O$ | — | — | 16.63 g in 200 ml $H_2O$ | 1.82 g in 200 ml $H_2O$ |

TABLE I-continued

|  | Ca(OH)$_2$ | Si(CH$_3$COO)$_4$ | MgCl$_2$ 6H$_2$O | Sr(NO$_3$)$_2$ | H$_3$PO$_4$ | NaHCO$_3$ |
|---|---|---|---|---|---|---|
|  |  |  | Concentr. range of reagents |  |  |  |
|  | 10-1000 g/l pref.: 30-250 g/l | 2-500 g/l pref.: 8-70 g/l | 5-700 g/l pref.: 25-250 g/l | 5-600 g/l pref.: 25-300 g/l | 5-1000 g/l pref.: 50-200 g/l | 2-600 g/l; pref.: 8-70 g/l |
| SiCHA-3 | 20 g in 600 ml H$_2$O | 1.94 g in 200 ml H$_2$O | — | — | 16.63 g in 200 ml H$_2$O | 4.00 g in 300 ml H$_2$O |
| SiMgHA-1 | 20 g in 600 ml H$_2$O | 1.94 g in 200 ml H$_2$O | 7.86 g in 200 ml H$_2$O | — | 16.63 g in 200 ml H$_2$O | — |
| SiMgCHA-1 | 20 g in 600 ml H$_2$O | 1.94 g in 200 ml H$_2$O | 7.86 g in 200 ml H$_2$O | — | 16.63 g in 200 ml H$_2$O | 8.12 g in 400 ml H$_2$O |
| SiMgCHA-2 | 20 g in 600 ml H$_2$O | 1.94 g in 200 ml H$_2$O | 7.86 g in 200 ml H$_2$O | — | 16.63 g in 200 ml H$_2$O | 1.82 g in 200 ml H$_2$O |
| SiMgCHA-3 | 100 g in 700 ml H$_2$O | 9.72 g in 200 ml H$_2$O | 39.30 g in 300 ml H$_2$O | — | 83.15 g in 300 ml H$_2$O | 9.09 g in 200 ml H$_2$O |
| MgHA | 100 g in 800 ml H$_2$O | — | 45.97 g in 200 ml H$_2$O | — | 88.8 g in 600 ml H$_2$O | — |
| SrMgHA-1 | 100 g in 600 ml H$_2$O | — | 45.97 g in 200 ml H$_2$O | 54.25 g in 200 ml H$_2$O | 88.8 g in 600 ml H$_2$O | — |
| SrMgHA-2 | 100 g in 600 ml H$_2$O | — | 65.13 g in 200 ml H$_2$O | 54.25 g in 200 ml H$_2$O | 88.8 g in 600 ml H$_2$O | — |
| SrMgHA-3 | 100 g in 600 ml H$_2$O | — | 86.83 g in 200 ml H$_2$O | 54.25 g in 200 ml H$_2$O | 88.8 g in 600 ml H$_2$O | — |
| SrSiMgCHA | 20 g in 600 ml H$_2$O | 1.94 g in 200 ml H$_2$O | 7.86 g in 200 ml H$_2$O | 8.22 g in 200 ml H$_2$O | 16.63 g in 200 ml H$_2$O | 1.82 g in 200 ml H$_2$O |

After dripping the solution of orthophosphoric acid (and of sodium bicarbonate, if desired) into the suspension of calcium hydroxide, added with silicate and/or Sr$^{2+}$, (and Mg$^{2+}$, if desired) ions, the resulting mixture is left under stirring for 1 h and then to rest for 2 h. The mother liquor is then removed, for instance by centrifugation (e.g. at 5000 revolutions for 3 minutes). The solid part is preferably redispersed in distilled water and then centrifuged again. This washing operation can be repeated several times, if desired. At the end of it, the powder is dried (for instance by freeze-drying or drying in a ventilated oven at 40-60° C.) and reduced to the desired granulometry for the following uses. In an embodiment of the invention, the powder of multi-substituted HA thus obtained is sieved to 150 μm.

By way of example, Table II contains comparative data of substitution molar ratios (substituent ion/substituted ion) used in some of the starting reagent solutions compared with those obtained in the corresponding synthesized powders of multi-substituted HAs, with the corresponding substitution yields.

In its turn, Table III contains the chemical composition of the compounds of Table II (content in wt % of concerned substituent ions).

TABLE III

|  | % by weight of substituent ions in hydroxyapatite | | | |
|---|---|---|---|---|
|  | Si | CO$_3$ | Mg$^{2+}$ | Sr$^{2+}$ |
| SiHA-1 | 0.63 | 2.48 | — | — |
| SiHA-2 | 1.26 | 2.41 | — | — |
| SiHA-3 | 2.41 | 2.35 | — | — |
| SiCHA-1 | <0.005 | 5.58 | — | — |
| SiCHA-2 | 0.41 | 4.13 | — | — |
| SiCHA-3 | 0.09 | 4.17 | — | — |
| SiMgHA-1 | 0.70 | 2.59 | 0.96 | — |
| SiMgCHA-1 | <0.005 | 3.15 | 2.97 | — |
| SiMgCHA-2 | 0.38 | 4.34 | 2.38 | — |
| SiMgCHA-3 | 0.42 | 4.87 | 1.08 | — |
| MgHA | — | 3.20 | 0.87 | — |

TABLE II

|  | Molar SiO$_4$/PO$_4$ | | | Molar CO$_3$/PO$_4$ | | | Molar Mg/Ca | | | Molar Sr/Ca | | |
|---|---|---|---|---|---|---|---|---|---|---|---|---|
|  | Reag. sol. | Subst. HA | Yield | Reag. sol. | Subst. HA | Yield | Reag. sol. | Subst. HA | Yield | Reag. sol. | Subst. HA | Yield |
| SiHA-1 | 0.050 | 0.040 | 0.80 | — | 0.065 |  | — | — |  |  |  |  |
| SiHA-2 | 0.100 | 0.081 | 0.81 | — | 0.066 |  | — | — |  |  |  |  |
| SiHA-3 | 0.200 | 0.163 | 0.81 | — | 0.069 |  | — | — |  |  |  |  |
| SiCHA-1 | 0.050 | <0.01 | 0.00 | 0.670 | 0.153 | 0.23 | — | — |  |  |  |  |
| SiCHA-2 | 0.050 | 0.026 | 0.64 | 0.150 | 0.112 | 0.75 | — | — |  |  |  |  |
| SiCHA-3 | 0.050 | 0.006 | 0.12 | 0.330 | 0.111 | 0.34 | — | — |  |  |  |  |
| SiMgHA | 0.050 | 0.045 | 0.90 | — | 0.069 |  | 0.150 | 0.040 | 0.27 |  |  |  |
| SiMgCHA-1 | 0.050 | <0.01 | 0.00 | 0.670 | 0.081 | 0.12 | 0.150 | 0.140 | 0.93 |  |  |  |
| SiMgCHA-2 | 0.050 | 0.025 | 0.50 | 0.150 | 0.118 | 0.79 | 0.150 | 0.104 | 0.69 |  |  |  |
| SiMgCHA-3 | 0.050 | 0.028 | 0.56 | 0.150 | 0.135 | 0.90 | 0.150 | 0.046 | 0.30 |  |  |  |
| MgHA | — | — | — | — | 0.087 |  | 0.150 | 0.043 | 0.29 | — | — | — |
| SrMgHA-1 | — | — | — | — | 0.090 |  | 0.150 | 0.061 | 0.41 | 0.20 | 0.083 | 0.41 |
| SrMgHA-2 | — | — | — | — | 0.093 |  | 0.200 | 0.078 | 0.39 | 0.20 | 0.085 | 0.42 |
| SrMgHA-3 | — | — | — | — | 0.094 |  | 0.250 | 0.126 | 0.50 | 0.20 | 0.091 | 0.45 |
| SrSiMgCHA | 0.050 | 0.014 | 0.28 | 0.150 | 0.098 | 0.65 | 0.150 | 0.093 | 0.62 | 0.20 | 0.08 | 0.42 |

TABLE III-continued

| | % by weight of substituent ions in hydroxyapatite | | | |
|---|---|---|---|---|
| | Si | $CO_3$ | $Mg^{2+}$ | $Sr^{2+}$ |
| SrMgHA-1 | — | 3.35 | 1.48 | 7.97 |
| SrMgHA-2 | — | 3.41 | 1.98 | 8.40 |
| SrMgHA-3 | — | 3.45 | 2.98 | 8.39 |
| SrSiMgCHA | 0.20 | 3.70 | 2.03 | 6.64 |

From Tables II and III it can be inferred, among other things, that hydroxyapatite substituted with silicate ions (SiHA), prepared as referred to above, has an effectiveness (yield) of molar substitution $SiO_4/PO_4$ of about 80%. During synthesis, carried out in air (non-inert atmosphere), it can be seen that powders incorporate from air small amounts of carbonate ions (Table II—SiHA; SiMgHA; MgHA; SrMgHA and Table III—2.35 to 3.45 wt %) into the phosphate site, whatever the content of silicate or $Sr^{2+}$ in the solution.

The degree of ion substitution inside the crystalline cell of HA is not always directly proportional to the amount of ion used as substituent reagent. This occurs especially with the synthesis of multi-substituted apatites, wherein the simultaneous presence of some ions can affect both positively and negatively the effectiveness and therefore the yield of substitutions.

Preferably, the process of synthesis is adjusted for each type of substitution by means of an iterative procedure (i.e. by carrying out a sufficient number of tests by varying repeatedly the mutual molar ratios between the reagent substituent ions). Thus, optimizing the amounts of initial reagents, it was possible to obtain the desired ion substitutions in the desired percentage.

It was thus possible to prepare multi-substituted hydroxyapatites characterized by the phosphate and calcium ion substitution ratios as described above.

Unexpectedly, the infrared spectroscopy analysis showed the absence of carbonation in site A of hydroxyapatite. The optimization of the preparation method according to the present invention as described above therefore enabled unexpectedly to obtain multi-substituted hydroxyapatites selectively carbonated in the phosphate site B of hydroxyapatite.

The substitution of $Ca^{2+}$ of hydroxyapatite with $Mg^{2+}$ was carried out to such an extent as to obtain a molar ratio $Mg^{2+}/Ca^{2+}$ of 0.01 to 0.30, corresponding to a percent molar ratio Mg/Ca of 1.00% to 30%; preferably in a molar ratio of 0.03 to 0.20, corresponding to a percent molar ratio Mg/Ca of 3% to 20%.

In the hydroxyapatite substituted with silicate and carbonate ions (SiCHA), the simultaneous substitution of silicate and carbonate ions in the phosphate site (site B) was evaluated by applying in the reagent solution a molar ratio $SiO_4/PO_4=0.05$ and a molar ratio $CO_3/PO_4$ of 0.15 to 0.67 (Table II). The result was that silicate does not appear in apatite structure if high carbonate concentrations ($CO_3/PO_4=0.67$) are present in the solution, whereas there can be a partial substitution of both ions if carbonate content in the solution is decreased. In particular, whereas the actual molar $CO_3/PO_4$ in the final powder (substituted HA) is of about 0.1, the content of $SiO_4$ actually substituting $PO_4$ strongly increases if the synthesis is carried out by applying in the starting solutions a molar ratio $CO_3/PO_4=0.15$ instead of =0.33. Similarly, whereas the carbonate fraction in the final powder is little above 4% by weight with respect to powder weight (100 g of synthetic powder contain 4 g of carbonate ions) in both cases, the weight percentage of $SiO_4$ changes from 0.1 to 0.4% (see Table III). Powders prepared by applying a starting molar ratio $CO_3/PO_4=0.15$ have a content of substituent ions similar to the amounts in biological tissues.

The effect of added carbonate in reducing the stability of hydroxyapatite is quite evident, since SiCHA-1, prepared using a molar $CO_3/PO_4$ of 0.67, consists of a low crystallinity apatite phase with small amounts of calcite, whereas in powders prepared applying molar ratios $CO_3/PO_4=0.15$ and 0.33, $CaCO_3$ is not formed. Silicate and carbonate co-substituted hydroxyapatite, SiCHA, is thermally highly stable with respect to silicate substituted hydroxyapatite, SiHA. As a matter of fact, after a thermal treatment at 1400° C., SiCHA apatite shows only small amounts of secondary phases, for instance beta tricalcium phosphate, β-TCP, about 1.5 vol % and, more rarely, CaO.

In the hydroxyapatite substituted with silicate and $Mg^{2+}$ ions (SiMgHA), under the above conditions of synthesis commonly applied, a certain amount of carbonate present in air and in the reaction environment spontaneously gets into the structure.

The substitution yield of the silicate ion, i.e. the amount that actually gets into HA structure with respect to the amount introduced into the reagent solution, expressed as molar ratio $SiO_4/PO_4$, is of 90%, whereas only about ⅓ of $Mg^{2+}$ introduced into the reagent solution (expressed as molar ratio Mg/Ca) is actually present in synthesized Subst. HA (Tables II and III).

Hydroxyapatites substituted with silicate, $Mg^{2+}$ and carbonate ions (SiMgCHA) were prepared by applying in the starting solutions molar ratios $SiO_4/PO_4=0.05$; $CO_3/PO_4=0.15-0.67$; Mg/Ca=0.15. Here again, high contents of carbonate in the solution ($CO_3/PO_4=0.67$) limit the incorporation of $SiO_4$ into the structure of HA. Under these conditions, carbonate itself shows a limited substitution yield (12%), but by applying a molar ratio $CO_3/PO_4=0.15$ between the reagent solution, it is possible to obtain in the multi-substituted synthetic hydroxyapatite incorporation yields up to 50% for silicate and up to 90% for carbonate, with a content in % by weight of carbonate in the final powder of 4.5-5%.

The effect of substituent ions in reducing the purity of hydroxyapatite is quite evident, as well as the crystallinity of the powder and the average crystalline size, because of the usually low crystallinity character of the resulting multi-substituted hydroxyapatite.

Whereas SiMgCHA apatite obtained by using a high initial content of carbonate in the solution (molar $CO_3/PO_4=0.67$) contains about 7% of calcite, by reducing the relative carbonate content to 0.15, apatite without secondary phases and stable up to 1000° C. is obtained, when traces of βTCP start appearing.

A positive effect was obtained also by increasing the concentration of $Ca^{2+}$ and of $PO_4^{3-}$ (and accordingly of all other reagents, so as to keep the same initial conditions as far as molar ratios are concerned) in the reagent solutions. As a matter of fact, the crystallinity of the powder and the effectiveness of substitution by foreign ions are affected. For instance, by changing from 20 g of $Ca(OH)_2$ (0.27 moles of $Ca^{2+}$) in a total volume of about 1000 ml of solution ($Ca(OH)_2$ concentration 20 g/l), to 100 g (1.28 moles of $Ca^{2+}$) in a total volume of about 1200 ml ($Ca(OH)_2$ concentration 83 g/l), and from 16.63 g of $H_3PO_4$ (0.14 moles of $PO_4$) in 200 ml ($H_3PO_4$ concentration 83.15 g/l) to 83.15 g (0.72 moles of $PO_4$) in 300 ml ($H_3PO_4$ concentration 277.17 g/l) (SiMgCHA-2 and SiMgCHA-3), while the content of $SiO_4$ in the corresponding synthetic apatites, Subst. HAs, is similar, the degree of carbonation increases and the content of $Mg^{2+}$ is almost halved.

It was observed that $Mg^{2+}$ succeeds in penetrating into these multi-substituted HAs in an amount of about 2.5-3% by weight, with respect to the weight of the synthetic powder, with a content of carbonate above 4% by weight with respect to the weight of the synthetic powder, and with a content of Si of about 0.4% by weight with respect to the weight of the synthetic powder. Here again, the simultaneous substitution of $SiO_4$ and carbonate ions was possible if the amount of carbonate introduced as reagent is 15% of the moles of phosphate.

The crystallinity and stoichiometry of Subst. HA powders strongly affect their thermal stability: for instance, SiMgCHA-2 and SiMgCHA-1 decompose thermally at 1000° C., while SiMgCHA-3 is quite stable, up to 1400° C. Hydroxyapatite substituted with $Sr^{2+}$, $Mg^{2+}$ and carbonate ions (SrMgCHA).

The evaluation of the effectiveness of the $Sr^{2+}$ ion as stabilizer of MgHA-apatite was made possible with the preparation of SrMgCHA. It is known that $Mg^{2+}$ penetrates with difficulty as substituent of $Ca^{2+}$ into the cell of hydroxyapatite, due to the great size difference between the two ions (ion radius $Ca^{2+}$=1.00 Å, ions radius $Mg^{2+}$=0.72 Å). The introduction of a bivalent cation with larger size such as $Sr^{2+}$ (ion radius $Sr^{2+}$=1.12 Å), which is present anyhow in physiological apatite, proved to be able to counterbalance the destabilizing effect of $Mg^{2+}$. The comparison of the chemical-physical properties of apatite powders obtained by syntheses with variable concentrations of $Mg^{2+}$ in the starting solution, in the presence or absence of $Sr^{2+}$ (the other process parameters remaining the same), enabled to observe that $Sr^{2+}$ can increase $Mg^{2+}$ incorporation into apatite. For instance, by using in the starting solution a percent molar ratio Mg/Ca of 15% an integration of $Mg^{2+}$ of 4.3 mol % (expressed as % Mg/Ca) and 0.87% by weight in the apatite powder in absence of strontium, to be compared with values of 6.1 mol % and 1.48% by weight, respectively, obtained by carrying out the synthesis in presence of $Sr^{2+}$ (Tables I and II: MgHA and SrMgHA-1 powders).

HAs co-substituted with $Sr^{2+}$ and $Mg^{2+}$ are resistant to heat treatment in air up to about 1000° C. without generating secondary phases, contrary to hydroxyapatite substituted with Mg only, which tends to turn into stoichiometric hydroxyapatite segregating Mg in the tricalcium phosphate phase. The possibility of co-substituting SrMgHAs with carbonate ions make them synthetisable under specific suitable conditions (carbon dioxide atmosphere, optimized thermal cycle) at relatively low temperatures with respect to stoichiometric HA, thus obtaining a good densification. It is thus possible to exploit as synergy the peculiar ability of $Sr^{2+}$ and the effect induced by a good densification in order to enhance the mechanical properties of apatite (which is important, for instance, for the production of porous bone substitutes).

Hydroxyapatite substituted with silicate, $Sr^{2+}$, $Mg^{2+}$, carbonate ions (SiSrMgCHA).

In a preferred embodiment of the invention, the synthesis of apatite referred to above, multi-substituted with contents of substituent ions within the biological range, was carried out by using preferably concentrations of the reagents in the solution such to obtain the following molar ratios: $SiO_4/PO_4$=0.05; $CO_3/PO_4$=0.15; Mg/Ca=0.15; Sr/Ca=0.20.

The final powder (Subst. HA) obtained is characterized by values of percent molar ratios $SiO_4/PO_4$=1.4%; $CO_3/PO_4$=9.8%; Mg/Ca=9.3%; Sr/Ca=8%, corresponding to a weight content of 0.20% silicate, 3.70% $CO_3$, 2.03% $Mg^{2+}$ and 6.64% $Sr^{2+}$.

To a merely indicative purpose, the multi-substituted non-stoichiometric hydroxyapatite according to the present invention can be averagely represented by the following formula:

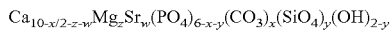
$$Ca_{10-x/2-z-w}Mg_zSr_w(PO_4)_{6-x-y}(CO_3)_x(SiO_4)_y(OH)_{2-y}$$

By mere way of example and without any limiting intent, an example of preparation of a particularly preferred multi-substituted hydroxyapatite according to the present invention is disclosed below.

Preparation of SrSiMgCHA (multi-substitution with four types of substituent ions).

The whole process is carried out at room temperature (25° C.)

A suspension of calcium hydroxide is prepared in a flask (capacity 2 liters) by dispersing 20 g of $Ca(OH)_2$ at 95% in 600 ml of $H_2O$. The resulting suspension is kept under stirring at about 300 rpm by means of a mechanical blade stirrer. Separately, the following solutions are prepared and added consecutively to the suspension of calcium hydroxide:

1.94 g of Si tetraacetate (purity 98%) in 200 ml of $H_2O$;
7.86 g of $MgCl_2.6H_2O$ (purity 99%) in 200 ml of $H_2O$;
8.22 g of $Sr(NO_3)_2$ (purity 99%) in 200 ml of $H_2O$.

Separately, the following solutions are prepared:
16.63 g of $H_3PO_4$ (purity 85%) in 200 ml of $H_2O$;
1.82 g of $NaHCO_3$ in 200 ml of $H_2O$.

These two solutions are added dropwise into the suspension of $Ca(OH)_2$, prepared previously, in about 3 hours, simultaneously but with separate feeders. Once the dripping is completed, the system is kept under stirring for 1 hour, then left to rest for one night. The supernatant liquor is then removed by centrifugation and three washing and centrifugation cycles, each with 1 l $H_2O$, are carried out. The product thus obtained is then dried in a ventilated oven (40° C.) (or by freeze-drying) and eventually sieved to 150 microns.

As was mentioned above, in all synthesized multi-substituted HAs according to the present invention there was no carbonation in site A (hydroxyl), thus confirming the effectiveness of the synthesis method according to the present invention in maximizing B-type carbonation (phosphate site).

All powders of multi-substituted HAs have nanometric size; the average particle size tends to decrease with the increase in the number of co-substitution. By way of example, for multi-substituted HA SiSrMgCHA average sizes of 20-25 nm were observed.

The X-Ray Diffractometry analyses (XRD) showed that all synthesized apatites are pure (i.e. without secondary phases) and characterized by a low degree of crystallinity, as a consequence of the optimal specific conditions of the process (reagents, temperature, ageing). XRD spectrums are very similar to the spectrum of the physiological inorganic phase.

More to this point, hydroxyapatites multi-substituted with at least three substituent ions proved to be particularly preferred as far as biomimetics and reabsorbability are concerned, i.e. the best similarity to the biological behavior of the apatite phase of natural bone tissue.

Hydroxyapatites multi-substituted with four substituent ions, as described above, proved to be still more preferred.

Density values of the powders of multi-substituted HA decrease from a value of 3.16 g/cm³, characterizing stoichiometric hydroxyapatite, the more co-substitutions are carried out, in accordance with the increase of structural defects and deviation from stoichiometry related thereto.

The effect of ion multi-substitution in HA on its solubility and therefore on its in-vivo reabsorbability was evaluated indirectly by measuring the conductivity of aqueous suspensions of the powders of said multi-substituted HA as a function of pH. Such analyses pointed out, as shown in the accompanying FIG. 1, that solubility varies according to the sequence SiHA<SiCHA, SiMgHA<SiMgCHA<SrSiMgCHA. Conductivity increases, starting from more basic pH values, according to the above sequence and, in particular, it can be observed that, anyhow, for all apatites, at physiological pH 7.4, the conductivity curve has risen from the plateau value, contrary to what occurs with a stoichiometric hydroxyapatite, which is almost insoluble (Kps about $10^{-56}$). Moreover, the absolute conductivity values of SiMgCHA and SrSiMgCHA are higher than those of other compared apatites, which makes them potentially more bioreabsorbable than the latter.

Direct tests of solubility of multi-substituted hydroxyapatites in a synthetic physiological fluid (Hank's balanced solution) basically confirm the above sequence, as well the consequent in-vivo improvement. This confirms what has been pointed out previously about the advantages related to synthetic hydroxyapatites multi-substituted with at least three substituent ions (preferably four) as far as their biomimetics and reabsorbability are concerned.

Multi-substituted HAs according to the present invention have proved extremely similar both structurally and biologically to physiologic HA present in bone tissues of the organism.

As a consequence, they represent the ideal synthetic substitute of physiological HA in the preparation of a completely biocompatible and biomimetic bone substitute.

To this purpose, in a particularly preferred embodiment of the present invention, the method for preparing multi-substituted HA according to the present invention is carried out in the presence of a convenient amount of a suitable natural and/or synthetic polymer; preferably, in the presence of collagen fibrils, simultaneously to the self-assembling process of said fibrils. It is thus possible to obtain a biohybrid composite material having a high compositional, morphological and structural biomimetics, since said composite is produced by simulating the osteogenesis process.

Therefore, a particularly preferred object of the present invention is the biohybrid composite referred to above, i.e. a substituted hydroxyapatite, as described above, said hydroxyapatite further comprising an effective amount of a biocompatible, natural or synthetic polymer (such as polylactic acid). Said polymer is preferably chosen among natural polymers of protein origin or polysaccharides: gelatins, albumins, alginates, gellan gum, starches, chitosans, celluloses, collagen and so on. More preferably, said natural polymer is collagen, in particular self-assembling collagen fibrils.

Said collagen is present in such an amount that the mutual weight ratio (w/w) of the final apatite inorganic phase, nucleated inside and on collagen fibrils, to collagen, SubstHA/Coll, is of about 85 to 15; preferably, said ratio is of 80 to 20; more preferably, of 75 to 25.

Still more preferred is a ratio SubstHA/Coll of about 70/30 w/w, which is near the weight/weight ratio biological apatite/organic component of bone tissue.

According to a preferential procedure, the desired amount of collagen is mixed with the solution of orthophosphoric acid. The resulting solution is dripped, if desired simultaneously to a solution of sodium bicarbonate (or another source of bicarbonate ions), into an aqueous suspension of calcium hydroxide, containing convenient amounts of silicate and/or $Sr^{2+}$ ions and, if desired, $Mg^{2+}$ ions, said ions being present in the ratios described above in the section concerning the preparation of multi-substituted HA powders according to the present invention. Said substituent ions mentioned above are present as water-soluble salts; preferably, as silicon tetraacetate, strontium nitrate, magnesium chloride or other similar salts.

At the end of dripping, which was carried out by using the same method as described previously, hydroxyapatite is formed (nucleated) inside and on the self-assembling collagen fibrils.

The biohybrid composite thus obtained is washed several times with water and lyophilized.

The biomimetics of the preparation method described above, and therefore of the bio-hybrid product obtained, can be optimized if said preparation is carried out under physiological conditions of temperature (37° C.) and pH (7.4) of the aqueous dispersing agent. In a particularly preferred embodiment, the synthesis is carried out using as solvent for the basic component, not pure water but synthetic physiological fluid (SBF) containing the same ions as are present in human plasma, and having pH=7.4 (physiological pH). Dilution conditions are critical for obtaining, as inorganic phase, pure substituted hydroxyapatite (i.e. not contaminated by other phases). Said conditions for an optimal dilution will be found experimentally every time, depending on the desired substitution quality and amount (here again an iterative process as the one described above is used).

The following contains, by mere way of non-limiting example, the preferred synthesis procedures of two composites multi-substituted HA/collagen in a ratio 70/30 weight/weight.

EXAMPLE 1

Preparation of Composite: SiMgCHA/Coll 70/30_SEF

Initial conditions (reagent solution)—the initial molar ratios are the following:
Molar ratio Mg/Ca=0.15;
Molar ratio $SiO_4/PO_4$=0.05;
Molar ratio $CO_3/PO_4$=0.15.
Operating Method:
An Aqueous solution A) is prepared, containing: 120 g of 1 wt % acetic collagen gel (corresponding to 1.2 g of collagen) added to a 85% solution of $H_3PO_4$ (0.0157 moles, corresponding to 1.809 g) in 250 ml of water.

An Aqueous solution B) is prepared, containing: $NaHCO_3$ (0.00141 moles, corresponding to 0.1184 g) in 100 ml of water.

An Aqueous suspension C) is prepared, containing the necessary amount of reagents for in-situ nucleation, inside and on collagen fibers, of 2.8 g of multi-substituted HA, i.e.:
95% $Ca(OH)_2$ (0.0279 moles, corresponding to 2.176 g) in 35 ml of SBF+700 ml of $H_2O$;
$MgCl_2.6H_2O$ (0.00487 moles, corresponding to 0.990 g) in 100 ml of $H_2O$;
98% $Si(CH_3COO)_4$ (0.000785 moles, corresponding to 0.218 g) in 100 ml of $H_2O$.

The two solutions A) and B) are dripped simultaneosly (preferably, separately) into the suspension C), kept under stirring at 37° C., in about 30-60 minutes.

At the end of addition, the mixture is left to rest for 1 h.

The supernatant liquor is removed by filtration (or centrifigation).

The composite is washed 3 times, each time with 300 ml of water.

The product is filtered and freeze-dried.

The product thus obtained has the following composition: molar Mg/Ca=0.052; molar $CO_3/PO_4$=0.135; molar $SiO_4/PO_4$=0.005

EXAMPLE 2

Preparation of Composite SrSiMgCHA/Coll 70/30_SBF

Initial conditions (reagent solution)—the initial molar ratios are the following:

Molar ratio Mg/Ca=0.15;

Molar ratio $SiO_4/PO_4$=0.05;

Molar ratio $CO_3/PO_4$=0.15;

Molar ratio Sr/Ca=0.20.

Operating Method:

An Aqueous solution A) is prepared, containing: 120 g of 1 wt % acetic collagen gel (corresponding to 1.2 g of collagen) added to a 85% solution of $H_3PO_4$ (0.0157 moles, corresponding to 1.809 g) in 250 ml of water.

An Aqueous solution B) is prepared, containing: $NaHCO_3$ (0.00141 moles, corresponding to 0.1184 g) in 100 ml of water.

An Aqueous suspension C) is prepared, containing the necessary amount of reagents for in-situ nucleation, inside and on collagen fibers, of 2.8 g of multi-substituted HA, i.e.:

95% $Ca(OH)_2$ (0.0279 moles, corresponding to 2.176 g) in 35 ml of SBF+700 ml of $H_2O$;

$MgCl_2.6H_2O$ (0.00487 moles, corresponding to 0.990 g) in 100 ml of $H_2O$;

$Sr(NO_3)_2$ (0.0058 moles, corresponding to 1.1807 g) in 100 ml of $H_2O$;

98% $Si(CH_3COO)_4$ (0.000785 moles, corresponding to 0.218 g) in 100 ml of $H_2O$.

The two solutions A) and B) are dripped simultaneosly (preferably, separately) into the suspension C), kept under stirring at 37° C., in about 30-60 minutes.

At the end of addition, the mixture is left to rest for 1 h. The supernatant liquor is removed by filtration (or centrifigation).

The composite is washed 3 times, each time with 300 ml of water.

The product is filtered and freeze-dried.

The product thus obtained has the following composition:
molar Mg/Ca=0.067; molar Sr/Ca 0.177; molar $CO_3/PO_4$=0.139, molar $SiO_4/Po_4$=0.006.

The composition of SBF used in Examples 1 and 2 is the following:

| Reagents | Moles/liter SBF |
|---|---|
| NaCl | 0.112 |
| $NaHCO_3$ | 0.027 |
| KCl | 0.005 |
| $Na_2HPO_4 \cdot 2H_2O$ | 0.0010 |
| $MgCl_2 \cdot 6H_2O$ | 0.0015 |
| $CaCl_2 \cdot 2H_2O$ | 0.0025 |
| $Na_2SO_4$ | 0.0005 |
| $(CH_2OH)_3CNH_2$ | 0.0501 |
| HCl | 0.0400 |

Similarly, the composites SiMgHA/Coll 70/30 and SrSiMgHA/Coll 70/30 were prepared by following the same experimental procedure, eliminating the intentional addition of carbonate ions and the use of SBF. The following molar ratios were obtained, respectively:

SiMgHA/Coll 70/30: molar Mg/Ca=0.066; molar $CO_3/PO_4$=0.05; molar $SiO_4/PO_4$=0.011.

SrSiMgHA/Coll 70/30: molar Mg/Ca=0.069; molar Sr/Ca=0.177; molar $CO_3/PO_4$=0.06; molar $SiO_4/PO_4$=0.011.

Moreover, the initial conditions of the reagents (molar ratios substituents of ions) were changed so as to obtain composites having different characteristics of biomimetics and reabsorbability, to be used to different purposes in different regeneration fields.

Table IV contains, by way of example, the data of the chemical analyses on some of the synthesized composites.

TABLE IV

| | Molar Mg/Ca | Molar Sr/Ca | Molar $SiO_4/PO_4$ | $CO_3$ wt %. in substituted hydroxyapatite |
|---|---|---|---|---|
| SiMgCHA/Coll 70/30 | 0.044-0.052 | — | 0-0.015 | >4 intentional introd. |
| SrSiMgCHA/Coll 70/30 | 0.052-0.067 | 0.149-0.187 | 0-0.015 | >4 intentional introd. |
| SiMgHA/Coll 70/30 | 0.054-0.066 | — | 0.011-0.05 | 2-3 spontaneous |
| SrSiMgHA/Coll 70/30 | 0.064-0.069 | 0.128-0.144 | 0.011-0.05 | 2-3 spontaneous |

The synthesized composites were analyzed from the compositional, chemical, physical, morphologic, structural points of view using the various analysis technics known in the field (for instance: ESEM (Environmental Scansion Electronic Microscopy), TEM (Transmission Electron Microscopy), XRD (X Ray Diffraction), FTIR (Fourier Transformed Infra Red Spectroscopy), STA (Simultaneous Thermal Analysis); EDS (Energy Dispersive Spectroscopy), as shown by way of example in the accompanying FIGS. 1-6).

Generally speaking, the following remarks can be made.

The introduction of carbonate ions into the synthesis limits the introduction of silicate ions into substituted HA.

In the preparation of the composite multi-substituted HA/collagen, it was possible to synthesize an apatite substituted with silicate ions (in phosphate position, site B) by limiting the content of carbonate ions which may become competing.

As a matter of fact, considering the composites SiMgHA/Coll 70/30 and SrSiMgHA/Coll 70/30 prepared without the intentional addition of carbonate ions, as previously disclosed, it was observed that, although a partial carbonation of the inorganic phase constituting the biohybrid composite spontaneously occurs in site B (as pointed out by the specific peaks in FTIR), with percent values within the range of biological carbonation, the introduction of silicate ions can be obtained under these conditions (Table IV). Therefore, it is preferable to use low initial amounts of carbonate (as already pointed out above for the preparation of substituted HAs not nucleated on collagen).

The ability of the $Sr^{2+}$ ion to promote a higher introduction of $Mg^{2+}$ ions into the structure, i.e. to increase the incorporation yield of $Mg^{2+}$, is confirmed.

The presence of $Sr^{2+}$ ions together with the $Mg^{2+}$ ion during synthesis enables to increase the stability of the apatite phase, i.e. to counterbalance the destabilizing effect induced per se by $Mg^{2+}$, and at the same time to increase the content of $Mg^{2+}$, which can be introduced into the inorganic phase, as was already pointed out in the synthesis of the inorganic phase only.

The development of synthetic multi-substituted apatites according to the present invention, with a complete, controlled level of ion substitutions in HA structure, has proved to be highly important since, as pointed out above, the behavior of the synthetic material thus obtained was optimally similar to the one of natural bone.

Said behavior, in particular from the point of view of reactivity, solubility, integration of the apatite implant, was due not only to the presence of the specific doping element/ion substituents in the material (and to their mutual amount), but also to the larger number of defects in the crystalline cell of multi-substituted HA, which defects are induced exactly by the very presence of the substituent ions.

The Applicant has advantageously found that the higher dissolution speed of the multi-substituted hydroxyapatite according to the present invention is related to a faster bone remodeling around the implant, with respect to stoichiometric hydroxyapatite. The increased reactivity with pre-existing bone has resulted in a higher stability in the implant site, thanks to the formation of a strong mechanical link between the implant and the surrounding area. Thus, rehabilitation time for the patient is reduced.

Moreover, by carrying out the nucleation of multi-substituted HAs according to the present invention on self-assembling, natural or synthetic organic templating materials (such as for instance self-assembling collagen fibrils), it was possible to obtain synthetic bone tissues, i.e. biohybrid composite materials having the same properties of natural bone tissues. Such biomimetics was ensured by the deep interaction occurring between inorganic and organic phase during the synthesis of the inorganic phase, thanks to a process simulating in-vivo the osteogenesis process.

The multi-substituted hydroxyapatite and the corresponding biohybrid composite thereof with collagen of suitable natural or synthetic polymers, according to the present invention, have therefore proved particularly advantageous in the preparation of a completely reabsorbable and biocompatible, biomimetic bone substitute.

An object of the present invention, therefore, is also the use thereof for preparing said bone substitute, as well as the bone substitute including them.

The invention claimed is:

1. An implantable biohybrid composite consisting of hydroxyapatite comprising phosphate ions and calcium ions partially substituted with different ion species, wherein said hydroxyapatite comprises:
   $Sr^{2+}$ ions in a molar ratio Sr/Ca of from 0.002 to 0.30; and
   $Mg^{2+}$ ions in a molar ratio Mg/Ca of from 0.01 to 0.20.

2. The implantable biohybrid composite according to claim 1, wherein the molar ratio Sr/Ca is from 0.02 to 0.30.

3. The implantable biohybrid composite according to claim 2, wherein the molar ratio Sr/Ca is from 0.03 to 0.25.

4. The implantable biohybrid composite according to claim 1, wherein the molar ratio Mg/Ca is from 0.03 to 0.20.

5. The implantable biohybrid composite according to claim 1, wherein the hydroxyapatite further comprises silicate ions in a molar ratio $SiO_4/PO_4$ of from 0.001 to 0.25.

6. The implantable biohybrid composite according to claim 5, wherein the molar ratio $SiO_4/PO_4$ of from 0.005 to 0.20.

7. The implantable biohybrid composite according to claim 6, wherein the molar ratio $SiO_4/PO_4$ of from 0.01 to 0.10.

8. The implantable biohybrid composite according to claim 1, wherein the hydroxyapatite further comprises $CO_3$ ions in a molar ratio $CO_3/PO_4$ of from 0.01 to 0.80.

9. An implantable biohybrid composite consisting of hydroxyapatite comprising phosphate ions and calcium ions partially substituted with different ion species, wherein said hydroxyapatite comprises:
   $Sr^{2+}$ ions in a molar ratio Sr/Ca of from 0.002 to 0.30;
   $Mg^{2+}$ ions in a molar ratio Mg/Ca of from 0.01 to 0.20; and
   a natural or synthetic polymer selected from the group consisting of: gelatins, albumins, alginates, gellan gum, starches, chitosans, celluloses, collagen, and polylactic acid.

10. The implantable biohybrid composite according to claim 1, wherein said hydroxyapatite is resistant to heat treatment in air up to about 1000° C. without generating secondary phase.

11. The implantable biohybrid composite according to claim 1, wherein the molar ratio Sr/Ca is from 0.002 to 0.25.

12. The implantable biohybrid composite according to claim 8, wherein the hydroxyapatite has a molar ratio $CO_3/PO_4$ from 0.05 to 0.30.

13. The implantable biohybrid composite according to claim 9, wherein the molar ratio Sr/Ca is from 0.02 to 0.30.

14. The implantable biohybrid composite according to claim 13, wherein the molar ratio Sr/Ca is from 0.03 to 0.25.

15. The implantable biohybrid composite according to claim 9, wherein the molar ratio Mg/Ca is from 0.03 to 0.20.

16. The implantable biohybrid composite according to claim 9, wherein the hydroxyapatite further comprises ions in a molar ratio $SiO_4/PO_4$ of from 0.001 to 0.25.

17. The implantable biohybrid composite according to claim 16, wherein the molar ratio $SiO_4/PO_4$ of from 0.005 to 0.20.

18. The implantable biohybrid composite according to claim 17, wherein the molar ratio $SiO_4/PO_4$ of from 0.01 to 0.10.

19. The implantable biohybrid composite according to claim 9, wherein the hydroxyapatite further comprises $CO_3$ ions in a molar ratio $CO_3/PO_4$ of from 0.01 to 0.80.

20. The implantable biohybrid composite hydroxyapatite according to claim 9, wherein the molar ratio Sr/Ca is from 0.002 to 0.25.

21. The implantable biohybrid composite hydroxyapatite according to claim 19, wherein the hydroxyapatite has a molar ratio $CO_3/PO_4$ from 0.05 to 0.30.

* * * * *